(12) United States Patent
Ku et al.

(10) Patent No.: US 7,833,483 B2
(45) Date of Patent: Nov. 16, 2010

(54) MESOPOROUS NANO-CRYSTALLINE TITANIA STRUCTURES FOR HYDROGEN SENSING

(75) Inventors: Anthony Yu-Chung Ku, Rexford, NY (US); Sergio Paulo Martins Loureiro, Saratoga Springs, NY (US); James Anthony Ruud, Delmar, NY (US)

(73) Assignee: General Electric Company, Niskayuna, NY (US)

( * ) Notice: Subject to any disclaimer, the term of this patent is extended or adjusted under 35 U.S.C. 154(b) by 548 days.

(21) Appl. No.: 11/777,305

(22) Filed: Jul. 13, 2007

(65) Prior Publication Data

US 2008/0011050 A1 Jan. 17, 2008

Related U.S. Application Data

(62) Division of application No. 10/993,569, filed on Nov. 18, 2004.

(51) Int. Cl.
*G01N 27/00* (2006.01)

(52) U.S. Cl. .............................. 422/98; 422/50; 422/83; 73/23.2; 977/953; 977/957

(58) Field of Classification Search ................... 422/57, 422/50, 83, 98; 9/57; 977/953, 957; 73/23.2
See application file for complete search history.

(56) References Cited

U.S. PATENT DOCUMENTS 7,282,259 B2 * 10/2007 Ku et al. .................. 428/307.7

OTHER PUBLICATIONS

Devi et al, "Synthesis of mesoporous TiO2-based powders and their gas-sensing properties", 2002, Sensors and Actuators B, 87, 122-129.*
Tacconi et al, "Semiconductor nanostructures in an alumina template matrix: microversus macro-scale photoelectrochemical behavior", 2002, Electrochimica Acta, 47, 2603-2613.*
Comini et al, "Sensitivity enhancement towards ethanol and methanol of TiO2 films doped with Pt and Nb", 2000, Sensors and Actuators B, 64, 169-174.*
Mor et al., "A Self-Cleaning, Room-Temperature Titania-Nanotube Hydrogen Gas Sensor", Sensor Letter, vol. 1, No. 1, pp. 42-46, 2003.
Varghese et al., "Extreme Changes in the Electrical Resistance of Titania Nanotubes with Hydrogen Exposure", Advanced Materials, vol. 15, No. 7-8, pp. 624-627, Apr. 17, 2003.

(Continued)

*Primary Examiner*—Lyle A Alexander
*Assistant Examiner*—Dennis M White
(74) *Attorney, Agent, or Firm*—Joseph J. Christian

(57) ABSTRACT

A structure includes a substantially non-conductive frame having an exterior surface. The structure defines a plurality of passages that open to the exterior surface. Mesoporous material is disposed in the plurality of passages and is supported therein by the frame. In a method for making a mesoporous nanocrystalline titania hybrid material, a templating agent, an acid, and a titania precursor is mixed into a template liquid. A frame that defines a plurality of passages is placed into the template liquid. A solvent is evaporated from the template liquid, thereby forming a titania gel encapsulating the templating agent. The gel is heated to remove substantially the templating agent from the non-conductive frame and the titania, thereby leaving a mesoporous titania material.

12 Claims, 4 Drawing Sheets

OTHER PUBLICATIONS

Mor et al., "A Room-Temperature TiO2-Nanotube Hydrogen Sensor Able to Self-Clean Photoactively From Environmental Contamination", J. Mater. REs., vol. 19, No. 2, pp. 628-634, Feb. 2004.

Wehrspohn et al., "Towards Ordered Porous Titania—A Comparison With Porus Alumina", Max-Planck-Institute of Microstructure Physics, Winberg 2, 06120 Halle, Germany, Department of Physics, University Paderborn, 33095 Paderborn, Germany, California Institute of Technoloy, Pasadena, CA 91125, 1 page. no date.

Choi et al., "Anodization of Nanoimprinted Titanium: A Comparison With Formation of Porous Alumina", Elsvier Electrochimica Acta, vol. 49, pp. 2645-2652, 2004.

* cited by examiner

US 7,833,483 B2

MESOPOROUS NANO-CRYSTALLINE TITANIA STRUCTURES FOR HYDROGEN SENSING

CROSS REFERENCE TO RELATED APPLICATIONS

This application claims the priority and benefit of U.S. patent application Ser. No. 10/993,569, entitled "MESOPOROUS NANO-CRYSTALLINE TITANIA STRUCTURES FOR HYDROGEN SENSING", filed on Nov. 18, 2004, which is incorporated herein by reference in its entirety.

BACKGROUND

1. Field of the Invention

The invention relates to nano scale structures and, more specifically, to a nano-crystalline titania structure that may be used in sensor applications.

2. Description of the Prior Art

Presently, hydrogen sensors employ electrochemical, optical or thermal detection methods. One system employs titania nanotubes arranged in an array. Such systems generally have pore sizes of greater than about 20 nm. Thus, the surface area of the sensing element is limited, thereby limiting performance indicia such as response and sensitivity. Recently, there has been renewed interest in metal oxide semiconductor-based devices. In titania, for example, the presence of hydrogen can dramatically change the resistivity of the material through a variety of physical mechanisms. The most common sensors depend on Schottky barrier modulation in structures with Pd or Pt electrodes. Present systems that utilize titania suffer from poor selectivity and slow response times.

Conventional microporous materials such as zeolites have regular pores with diameters of less than about 2 nm. Macroporous materials have pores greater than about 50 nm, but with widely varying pore sizes. Examples of well-known porous materials include activated carbon used in deodorizers and silica gel used in desiccants. The conventional porous materials with regular pore sizes, such as zeolites, have limitations in pore diameter size, while those with large pores have widely varying pore sizes. Mesoporous materials are porous materials with regularly arranged, relatively uniform mesopores (2 nm to 50 nm in diameter). They generally exhibit a large surface area.

Existing methods are limited by a combination of high cost, limited sensitivity, poor selectivity and slow response times. Contamination of the sample and subsequent performance degradation also limit existing systems use.

Therefore, there is a need for a hydrogen sensor that exhibits good selectivity and that has a quick response.

SUMMARY OF THE INVENTION

The disadvantages of the prior art are overcome by the present invention, which, in one aspect, is a structure that includes a substantially non-conductive frame having an exterior surface. The structure defines a plurality of passages that open to the exterior surface. Mesoporous material is disposed in the plurality of passages and is supported therein by the frame.

In another aspect, the invention is a sensor of a target substance in which a mesoporous titania material is disposed within a frame. The mesoporous titania material includes mesopores that are capable of receiving the target substance therein. The mesoporous titania is capable of interacting with the target substance and has a property that is a function of interaction with the target substance. A component senses a change in the property when the mesoporous nanocrystalline material is exposed to the target substance.

In yet another aspect, the invention is a method for making a mesoporous nanocrystalline titania hybrid material. A templating agent is mixed into a solvent and an acid to form a template liquid. A titania precursor is added to the template liquid. A substantially non-conductive frame having an exterior surface and defining a plurality of passages that open to the exterior surface is placed into the titania precursor and the template liquid. The titania precursor and the template liquid are allowed to infiltrate into the plurality of passages. The solvent is evaporated from the template liquid, thereby forming a titania gel encapsulating the templating agent. The gel is heated at a preselected temperature for a preselected period of time sufficient to remove substantially the templating agent from the non-conductive frame and the titania, thereby leaving a mesoporous titania material in the plurality of passages.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAILED DESCRIPTION OF THE INVENTION

Figure 1:
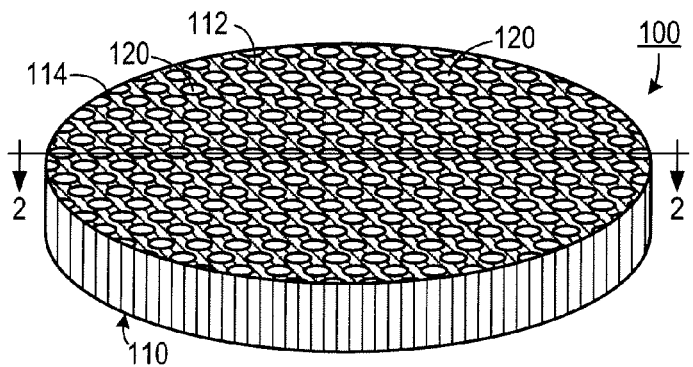
FIG. 1 is a top perspective schematic view of an exemplary embodiment of the invention.

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Unless otherwise specified herein, the drawings are not necessarily drawn to scale. Also, as used herein "mesoporous nanocrystalline hybrid material" refers to a porous material with nanoscale crystals and an amorphous matrix. Diameters of pores and passages listed herein refer to average diameters to provide for eccentricity.

As shown in FIG. 1, one illustrative embodiment includes a structure 100 that includes a substantially non-conductive frame 110. The frame 110 has at least one exterior surface 114 and defines a plurality of passages 120 that open to the exterior surface 114. The frame 110 could, for example, include an anodic aluminum oxide membrane 112.

Figure 2:
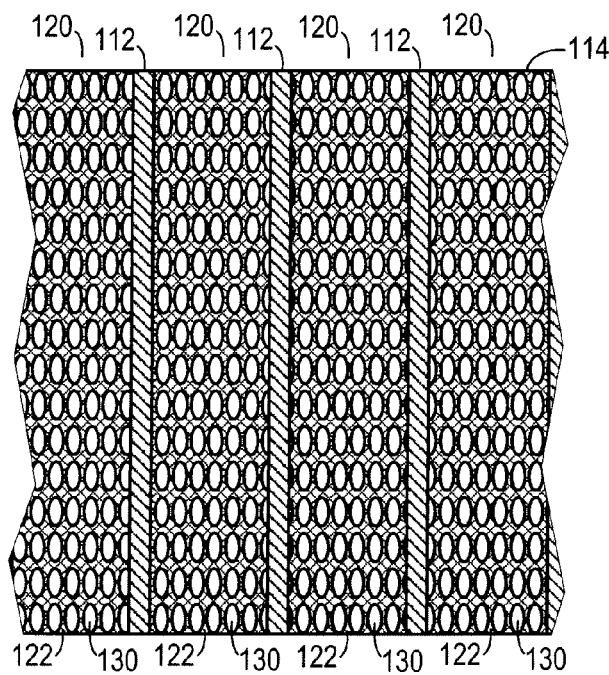
FIG. 2 is a cross-sectional view of the embodiment shown in FIG. 1, taken along line 2-2.

As shown in FIG. 2, mesoporous material 122 is disposed in the plurality of passages 120 and is supported therein by the frame 110. The mesoporous material 122 includes a matrix, such as a titania matrix, and a plurality of mesopores 130 that are in fluid communication with the exterior surface 114. The titania matrix may be crystalline, amorphous or a hybrid of the amorphous and nanocrystalline material. Typically, the passages 120 will have a diameter in a range of between 20 nm to 210 nm, with a range of between 10 nm to 300 nm being possible. Depending on the size of the passages 120 and other process-related factors, the mesopores 130 will typically have a diameter in the range of between 2 nm to 50 nm.

Figure 3A:
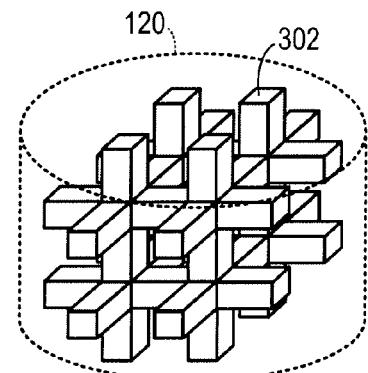
FIG. 3A is a schematic illustration of mesopores in a cubic arrangement.
Figure 3B:
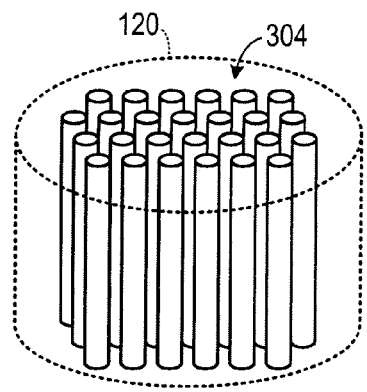
FIG. 3B is a schematic illustration of mesopores in a hexagonal arrangement.

As shown in FIG. 3A, the mesopores 302 may be exhibit a cubic ordering. As shown in FIG. 3B, the mesopores 304 may also exhibit a hexagonal ordering. As would be clear to those of skill in the art, other orderings are possible and would fall within the scope of the invention.

Figure 4:
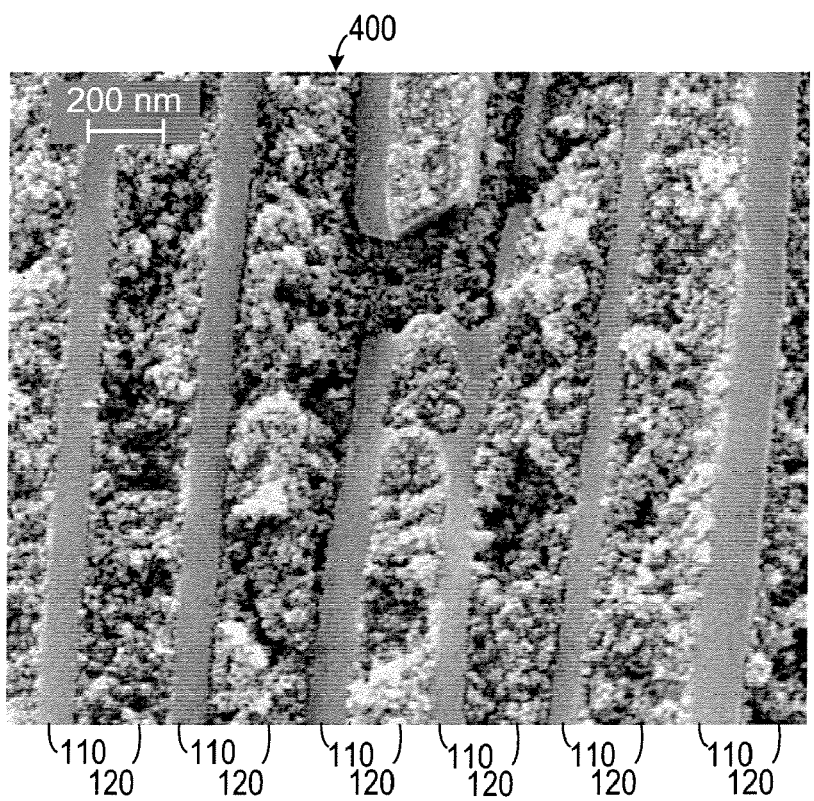
FIG. 4 is a micrograph of a cross-section of a mesoporous structure.
Figure 5:
FIG. 5 is a micrograph of an ordered mesoporous structure.

A micrograph 400 of a cross-section of one experimental embodiment is shown in FIG. 4. In this micrograph, one can see vertical walls of the frame 110 and the passages 120 filled with mesoporous material. A micrograph 500 of a passage with highly ordered mesopores is shown in FIG. 5.

Figure 6:
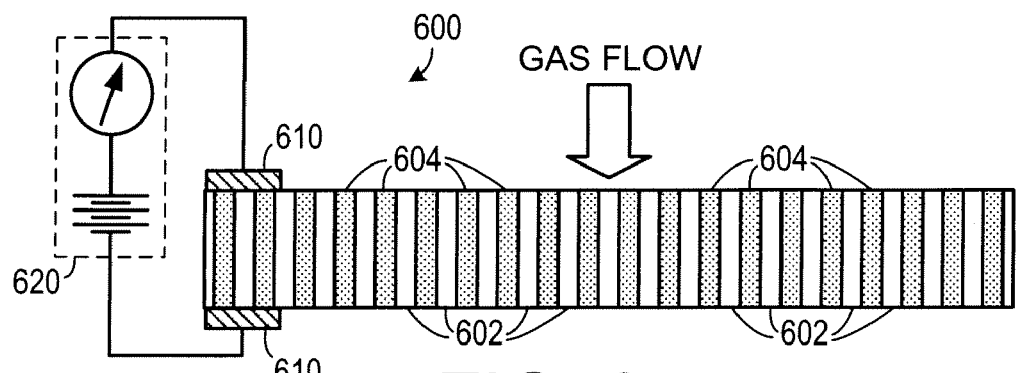
FIG. 6 is a cross-sectional schematic illustration of a gas sensor employing a mesoporous structure.

One embodiment of a hydrogen sensor 600 employing mesoporous material is shown in FIG. 6. Mesoporous titania 604 is disposed within an anodic aluminum oxide frame 602. Hydrogen received in the mesopores interacts with the mesoporous titania defining the mesopores. The mesoporous titania has an electrical resistance that is a function of interaction with hydrogen. A resistance sensor 620, that is electrically coupled to the mesoporous titania 604 through a pair of contacts 610 (such as platinum contacts) senses a change in the resistance of the mesoporous titania 604 when it is exposed to hydrogen.

Figure 7A:
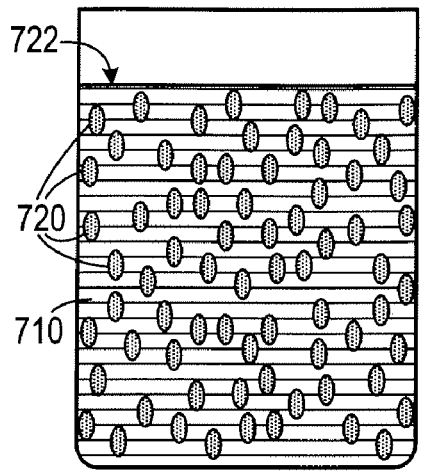
FIGS. 7A-7F are schematic diagrams showing steps executed in one method of making a mesoporous structure.
Figure 7B:
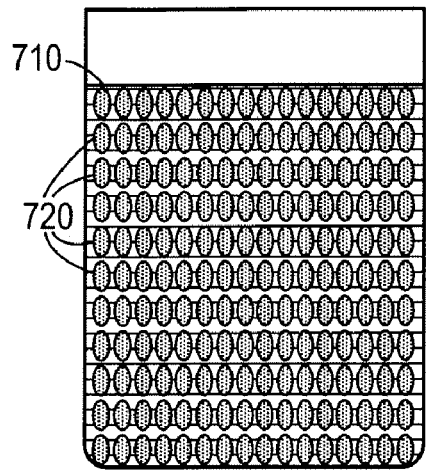

As shown in FIGS. 7A through 7F, one illustrative method for making a structure, as disclosed above, includes mixing a templating agent 720 into a solution 710 of a solvent and an acid to form a template liquid 722. A titania precursor is added to the template liquid 722. The templating agent 720 may self-assemble to form an ordered arrangement, as shown in FIG. 7B.

Figure 7C:
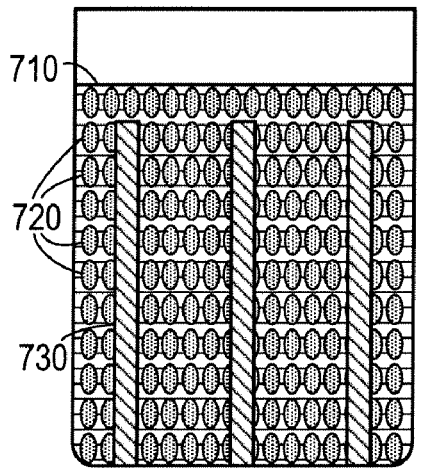

An anodic aluminum oxide membrane 730, or other substantially non-conductive frame that defines a plurality of passages, is placed in the titania precursor and the template liquid 722. The template liquid and titania precursor are allowed to infiltrate into the plurality of passages of the anodic aluminum oxide membrane 730, as shown in FIG. 7C.

Figure 7D:
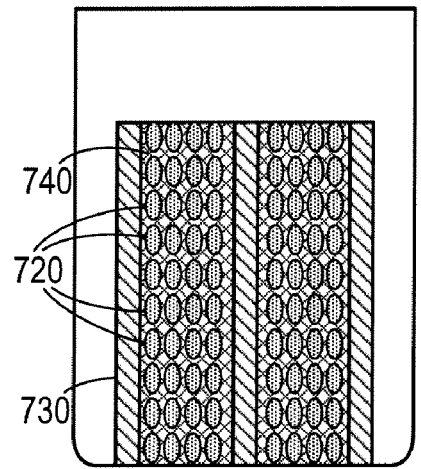
Figure 7E:
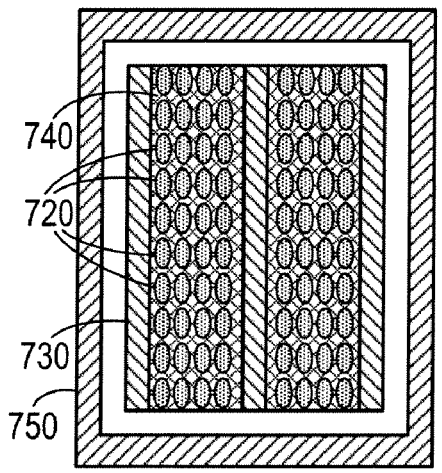
Figure 7F:
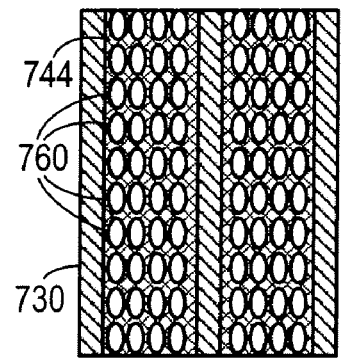

The solvent is allowed to evaporate from the template liquid, thereby forming a titania gel 740 encapsulating the templating agent 720, as shown in FIG. 7D. As shown in FIG. 7E, the gel 740 is heated in an oven 750 for enough time and at a high enough temperature to remove substantially all of the templating agent from the non-conductive frame and the titania (either through vaporization or oxidation), thereby leaving a plurality of mesopores 760 in a matrix of titania 744. Examples of templating agents include: a non-ionic block copolymer (e.g., polyethylene oxide-polypropylene oxide-polyethylene oxide, including Pluronic type P123, F127, F108, F88), a cationic surfactant, an anionic surfactant, a zwritterionic surfactant, a non-ionic surfactant, or a combination thereof. Examples of titania precursors include titanium ethoxide, titanium chloride, titanium isopropoxide, titanium butoxide, titanium methoxide, titanium propoxide, or a combination thereof. In one experimental example, the gel was heated in air at 400° C. for 10 hours. The resulting mesoporous titania was then allowed to cool at a rate of 60° C. per hour after completion of the heating step.

A dopant may be added to the solvent to achieve certain desired physical properties. For example, dopants may be added to make sensors directed to a specific element, or to fine tune the sensitivity of a sensor to specific concentration ranges. Examples of suitable dopants include: Ce, Co, Fe, Mn, N, Nd, Pd, Pt, S, V, W, Eu, Cr, Tb, Er, Pr, and combinations thereof. Dopants such as Ce, Co, Fe, Mn, N, Nd, Pd, Pt, S, V, W may be useful in fabrication of electrical sensors, whereas dopants such as Eu, Cr, Tb, Er, Pr, Mn and Nd may be useful in optical sensors using mesoporous titania. Such an optical sensor could measure phosphorescence or work according to an interferometric sensor model. Possible mechanisms for changing an optical property in doped mesoporous titania include the following: direct adsorption in which a monolayer on the surface changes the index of refraction; coordination number change from adsorption; change in oxidation state; change in crystal field strength; and change in hydration state.

One embodiment of the invention uses a mesoporous nanocrystalline titania structure as the sensing element for hydrogen. The mesoporous character of the porosity provides a large surface area for interaction between the hydrogen and the titania. This embodiment employs thin film configurations, which can improve the response time of the sensor. (Thinner films reduce the time needed for gas diffusion and also decrease the electrical path length in the titania structure.) Sensing elements fabricated within larger pores of a template such as anodic aluminum oxide offer the benefit of access to $H_2$ from both sides of the sensor, effectively reducing the thickness by half, and simplifying integration into devices.

The use of mesoporous nanocrystalline titania also addresses the sensitivity issue by using the a detection mechanism similar to that observed in nanotubes. The thickness of the nanocrystalline walls is comparable (about 2-10 nm), but the pore diameter is much smaller (about 10 nm versus 20-100 nm). This higher effective packing leads to a greater degree of sensitivity.

Doping of the titania with luminescent species can also lead to improvements in the selectivity and response time. The synthesis method used for these structures easily accommodates doping. Surface modification of the titania mesopores with a material catalytic for $H_2$ such as Pd and Pt offers the potential to increase the response time of the sensor by increasing the adsorption kinetics.

Titania is known to exhibit a photocatalytic effect when exposed to light with an energy higher than its bandgap. Practically, this means it is possible to regenerate a titania structure that has been fouled by an organic by exposing the system to UV light. This would generate radicals at the surface of the titania which would oxidize the organic substance. The rate of self-cleaning would depend on the photocatalytic activity of the titania, the incident UV intensity, and the time of UV exposure.

In one illustrative example, a mesoporous titania sensor was fabricated using the following steps. A precursor solution was prepared by first completely dissolving 1.5 g of P123 block copolymer in 24 g of ethanol. The solution was then poured into a Petri dish, containing several elastomer spacers. The spacers were completely submerged after adding the precursor solution. An anodic aluminum oxide membrane (referred to herein as "AAO," 25 mm diameter, 50 μm thick, with 200 nm pores) was immersed horizontally in the fluid on top of the spacers. The AAO used was an ANODISC inorganic membrane available from Whatman International Ltd. of Florham Park, N.J. (4) The solvent was allowed to evaporate at room temperature for 20 hours. During this time, the fluid level in the dish dropped below the level of the AAO membrane due to evaporation of the volatile components. The AAO membrane was removed from the spacers and heated in air at 400° C. for about 10 hours. The heating and cooling rate was 60° C. per hour. Electrical contact pads were fabricated on the top and bottom surfaces of the membrane using a Pt powder paste and firing at 400° C. for 1 hour. Pt lead wires were bonded to the Pt contact pads using Ag paste. The sample was placed in a gas-tight tube through which $N_2$ gas and a mixture of $H_2/N_2$ gases could be introduced, and the electrical resistance was measured using an ohm-meter. $N_2$ was introduced at a rate of 200 sccm (standard cubic centimeters per minute) and a resistance of about 14-15 megaohms was observed. A 4% $H_2/N_2$ gas mixture was added at a rate of 5 sccm to the flow to make a mixture of 975 ppm $H_2$ in $N_2$. After 10 minutes, the resistance dropped to about 5 megaohms. The flow of the $H_2/N_2$ mixture was stopped and after 5 minutes the resistance reverted back to a high value of about 16 mega-ohms.

Figure 8:
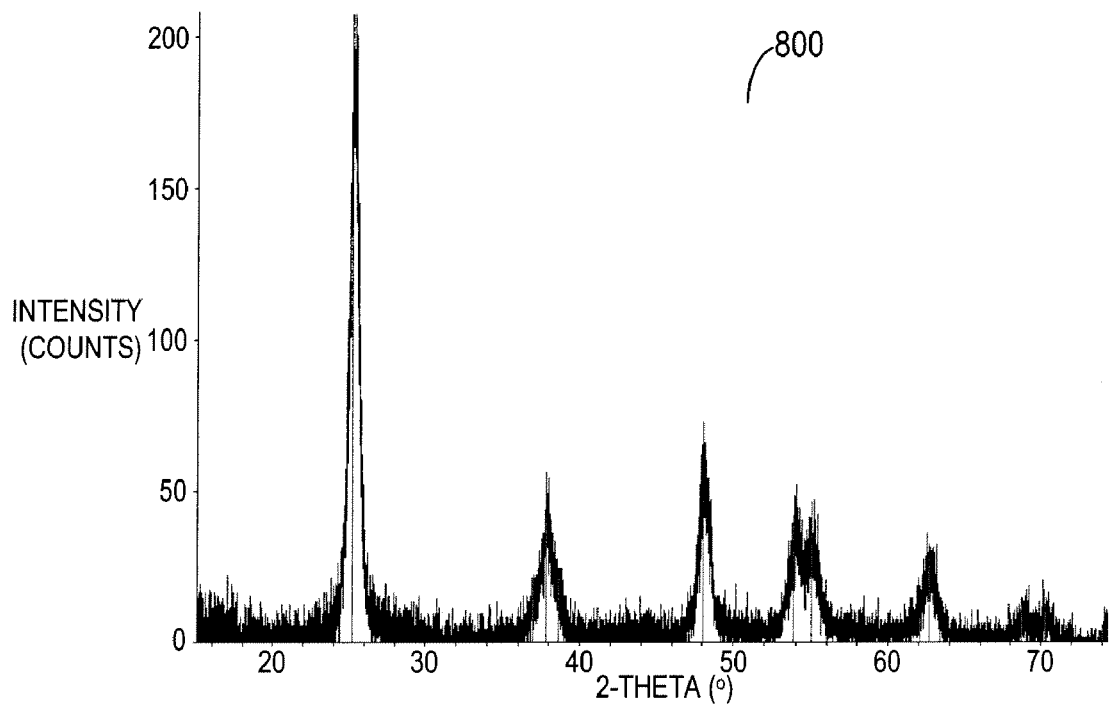
FIG. 8 is a graph of x-ray diffraction intensity of an experimental sample of mesoporous material.
Figure 9:
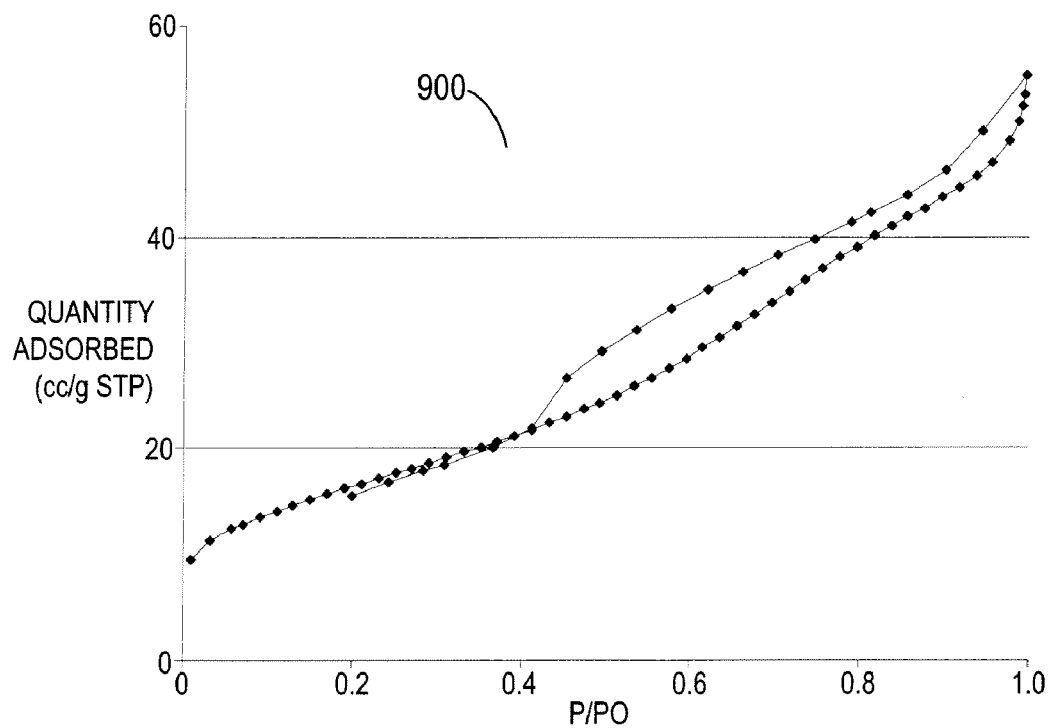
FIG. 9 is a nitrogen adsorption graph of one experimental sample.

FIG. 8 shows an x-ray diffraction pattern 800 of one experimental sample of mesoporous material. The peaks are indexable to the anatase phase and the peak broadening indicates nanometer-sized crystallites. As shown in FIG. 9, a nitrogen adsorption-desorption isotherm 900 of one experimental sample was measured at 77 K. The hysteresis is typical of a type IV isotherm and indicates mesoporosity. The BET surface area of the sample, as fitted from the data, is about 40 $m^2/g$.

The above described embodiments are given as illustrative examples only. It will be readily appreciated that many deviations may be made from the specific embodiments disclosed in this specification without departing from the invention. Accordingly, the scope of the invention is to be determined by the claims below rather than being limited to the specifically described embodiments above.

What is claimed is:

1. A sensor of a target substance, comprising:
   a mesoporous material disposed within a plurality of passages of a substantially non-conductive frame, the mesoporous material comprising a titania matrix and a plurality of mesopores that are in fluid communication with an exterior surface of the frame so as to be capable of interacting with and receiving the target substance therein, the mesoporous material having a property that changes when exposed to the target substance; and
   a component that senses the change in the property of the mesoporous material when the mesoporous material is exposed to the target substance,
   wherein at least some of the mesopores exhibit a cubic ordering.

2. The sensor of claim 1, wherein the target substance comprises hydrogen.

3. The sensor of claim 1, wherein the property comprises an electrical resistance.

4. The sensor of claim 1, wherein the frame comprises anodic aluminum oxide.

5. The sensor of claim 4, wherein the frame comprises an anodic aluminum oxide membrane.

6. The sensor of claim 1, wherein the plurality of mesopores has a diameter in a range of between 2 nm and 50 nm.

7. The sensor of claim 1, wherein the mesoporous material comprises nanocrystals.

8. The sensor of claim 1, wherein the mesoporous material comprises a hybrid of nanocrystalline material and amorphous material.

9. The sensor of claim 1, further comprising a dopant added to the mesoporous material.

10. The sensor of claim 9, wherein the dopant is selected from a group consisting of Ce, Co, Fe, Mn, N, Nd, Pd, Pt, S, V, W, or combinations thereof.

11. The structure of claim 1, wherein the titania matrix is selected from a group consisting of a crystalline material, an amorphous material, or a combination thereof.

12. A sensor of a target substance, comprising:
   a mesoporous material disposed within a plurality of passages of a substantially non-conductive frame, the mesoporous material comprising a titania matrix and a plurality of mesopores that are in fluid communication with an exterior surface of the frame so as to be capable of interacting with and receiving the target substance therein, the mesoporous material having a property that changes when exposed to the target substance; and
   a component that senses the change in the property of the mesoporous material when the mesoporous material is exposed to the target substance,
   wherein at least some of the mesopores exhibit a hexagonal ordering.

* * * * *